United States Patent [19]
Wright

[11] Patent Number: 6,039,175
[45] Date of Patent: Mar. 21, 2000

[54] MULTI-POCKET FEMALE WALLET

[76] Inventor: Russel Wright, 3412 N. 48th St., Milwaukee, Wis. 53216

[21] Appl. No.: 09/167,247

[22] Filed: Oct. 6, 1998

Related U.S. Application Data

[63] Continuation-in-part of application No. 08/777,529, Dec. 30, 1996, abandoned.

[51] Int. Cl.⁷ .............................. A45C 1/06; A45C 11/26
[52] U.S. Cl. ............................ 206/37; 150/131; 150/143; 383/39
[58] Field of Search ..................................... 150/140, 131, 150/132, 143; 383/38–40; 206/37

[56] References Cited

U.S. PATENT DOCUMENTS

| | | | |
|---|---|---|---|
| 2,592,046 | 4/1952 | Leue et al. | 150/132 |
| 4,209,048 | 6/1980 | Sandos | 150/132 |
| 4,738,547 | 4/1988 | Brown | 383/40 X |
| 4,779,655 | 10/1988 | Olson | 383/40 X |
| 4,911,178 | 3/1990 | Neal | 150/131 X |
| 4,930,635 | 6/1990 | Hotchkiss | 150/131 X |
| 5,002,401 | 3/1991 | Blackman | 190/901 X |
| 5,165,544 | 11/1992 | Gusenoff et al. | 383/40 X |
| 5,263,523 | 11/1993 | Scheunemann | 150/132 |
| 5,577,607 | 11/1996 | Drake et al. | 383/40 X |
| 5,778,954 | 7/1998 | Sullivan et al. | 150/132 X |

*Primary Examiner*—Sue A. Weaver
*Attorney, Agent, or Firm*—Donald J. Ersler

[57] ABSTRACT

A multi-pocket female wallet includes a cover, and a plurality of pockets. The cover comprises an outside layer, and an inside layer having the shape of a rectangle. A first end of a pocket template is cut into the shape of three equally spaced apart tab projections. The plurality of tab projections are folded over the bottom folded member. The cover is fastened to the pocket template at the top edge thereof. A first and second stitch create three pockets in the pocket template. The plurality of tab projections are attached to the bottom folded member with suitable fastening means. A second embodiment of a multi-pocket female wallet includes a cover, a pocket member, and an attachment strap. The cover has a plurality of layers which are attached to the pocket member with a surrounding seam binding. Pockets are defined by sewing the cover to the pocket member substantially perpendicular to the length of the pocket member. The second embodiment of the multi-purpose female wallet is preferably folded into three sections and retained in a folded position by fastening the attachment strap.

14 Claims, 4 Drawing Sheets

MULTI-POCKET FEMALE WALLET

CROSS-REFERENCE TO RELATED APPLICATIONS

This is a continuation-in-part application of Ser. No. 08/777,529 filed on Dec. 30, 1996, now abandoned.

BACKGROUND OF THE INVENTION

1. Field of the Invention

The present invention relates generally to wallets and more specifically to a multi-pocket female wallet which is capable of holding a plurality of female sanitary devices such as tampons and sanitary napkins in a convenient and tasteful manner.

2. Discussion of the Prior Art

Women often have the necessity for carrying sanitary napkins or tampons with them. The sanitary napkin or tampon is usually stored in a purse when a woman goes out of her home. Unfortunately, if the woman is with friends or around others, she will have to lug a purse with her to the bathroom, or possibly suffer embarrassment by exposing the sanitary napkin or tampon to inquiring eyes. Further, women usually have a myriad of items stored inside their purses which may damage a sanitary napkin or tampon while the purse is being transported.

Accordingly, there is a clearly felt need in the art for a multi-pocket female wallet which is capable of holding a plurality of sanitary napkins or tampons. The multi-pocket female wallet can act as its own tasteful carrying case for retaining a plurality of sanitary napkins or tampons while protecting them from damage that may result from transport in a purse.

SUMMARY OF THE INVENTION

The primary objective of the present invention is to provide a multi-pocket female wallet which is capable of holding a plurality of sanitary napkins or tampons. The multi-pocket female wallet can act as its own tasteful carrying case for retaining a plurality sanitary napkins or tampons while protecting them from damage that may result from storage in a purse.

According to the present invention, a multi-pocket female wallet includes a cover, and a plurality of pockets. The cover includes an outside layer and an inside layer, both having the shape of a rectangle. The ends of the cover are folded over to form a border of about 5/16 of an inch around the perimeter. A top folded end is created by folding the top end of the cover over. A bottom folded end is created by folding the bottom end of the cover over. The top folded end is folded toward the bottom folded end to form an inside layer and outside layer. The folded over ends of the outside layer and inside layer are joined together. The outside layer and inside layer are sewn together with a piece of thread such that the thread is disposed about 3/32 of an inch inward from the perimeter of the outside and inside layer. The outside and inside layer may also be fastened together with heat staking or glue.

The plurality of pockets are fabricated from a pocket template. A first end of the pocket template is cut into the shape of at least three tab projections which are equally spaced apart to form a plurality of pockets. A second end of the pocket template has a plurality of recesses which are equally spaced apart. The second end is folded over toward the first end to form a bottom folded member. The plurality of tab projections are folded over the bottom folded member of the pocket template.

The plurality of pockets are formed by folding over the top edge of the cover about ½ of an inch, slipping the top edge of the pocket template under the top edge of the cover, and sewing the cover and top edge of the pocket template together. The pocket template may also be fastened to the cover with heat staking or glue. A left edge of the plurality of pockets are sewn to a left edge of the cover. A right edge of the plurality of pockets are sewn to a right edge of the cover. The pocket template may also be fastened to the cover at the left and right edges with heat staking or glue, The plurality of tab projections are folded back, and three equally spaced apart pockets are formed in the pocket template by sewing two equally spaced apart stitches through the pocket template and cover. The pockets may also be formed by heat staking.

The following hook fasteners loop fasteners may be sold under the registered trademark, "Velcro." A hook fastener pad is attached to an end of each tab projection. A loop fastener pad is attached to the respective location on the bottom folded member such that the plurality of tab projections are attached to the bottom folded member of the pocket template. The left edge of the cover is folded toward the right edge such that an one-third length of the cover is folded over to form a left folded member. A hook fastener pad is attached to the right edge of the cover. The right edge of the cover is folded over the left edge such that an one-third length of the cover is folded over the left edge to form a right folded member. A loop fastener pad is fastened to the respective location on the left folded member such that the right folded member may be attached to the left folded member.

A second embodiment of a multi-pocket female wallet includes a cover, a pocket member, and an attachment strap. The cover includes two outside layers and an inside layer. The outside edges of the outside layers, inside layer, and pocket member are attached together with a surrounding seam binding. The top edge of the pocket member is terminated with a top edge seam binding. Pockets are defined by sewing the cover to the pocket member substantially perpendicular to the length of the pocket member. The attachment strap is attached to an end of the cover. Preferably, a loop fastener pad is attached to an end of the attachment strap and a hook fastener pad is attached to the side opposite the pocket member. The multi-purpose female wallet is preferably folded into three substantially equal sections. The folding areas are defined by the location of the substantially perpendicular sewing in the pocket member. The multi-purpose female wallet is retained in a folded position by attaching the end of the attachment strap to the hook fastener pad.

Accordingly, it is an object of the present invention to provide a multi-pocket female wallet which can hold a plurality of sanitary napkins and tampons.

It is a further object of the present invention to provide a multi-pocket female wallet which can serve as an attractive and convenient carrying case for a plurality of sanitary napkins and tampons.

It is yet a further object of the present invention to provide a multi-pocket female wallet which may be easily folded together when different items are stored therein.

Finally, it is another object of the present invention to provide a multi-pocket female wallet which protects a plurality of sanitary napkins and tampons from damage while stored in a purse.

These and additional objects, advantages, features and benefits of the present invention will become apparent from the following specification.

DETAILED DESCRIPTION OF THE PREFERRED EMBODIMENTS

Figure 1:
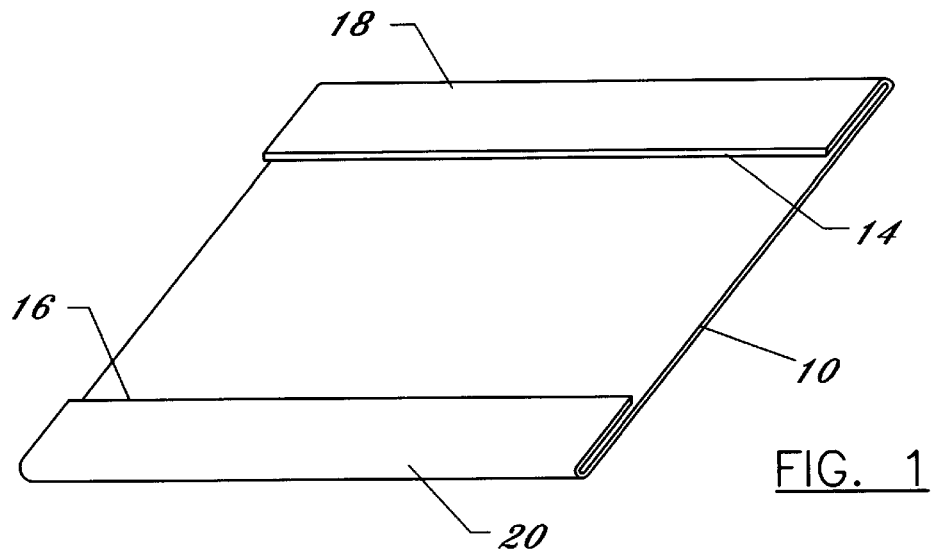
FIG. 1 is a perspective view of a cover of a multi-pocket female wallet with a top and bottom end folded over in accordance with the present invention.
Figure 2:
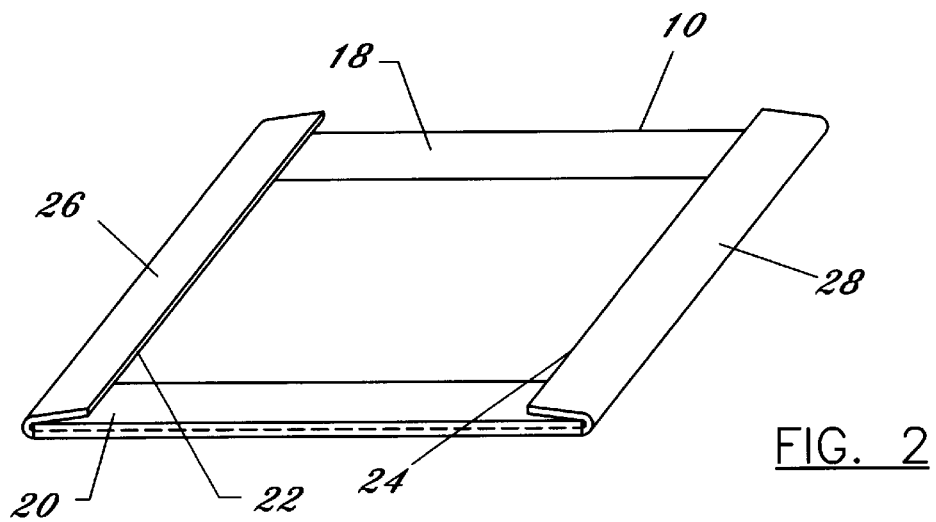
FIG. 2 is a perspective view of a cover of a multi-pocket female wallet with a left and right end folded over in accordance with the present invention.

With reference now to the drawings, and particularly to FIG. 1, there is shown a perspective view of a cover 10 with a top end 14 and a bottom end 16 folded over. The width of a top folded end 18 and a bottom folded end 20 can be within the range of 3/16 to 1/2 of an inch. FIG. 2 shows a perspective view of a cover 10 with a left end 22 and a right end 24 folded over. The width of a left folded end 26 and a right folded end 28 can be within the range of 3/16 to 1/2 of an inch.

Figure 3:
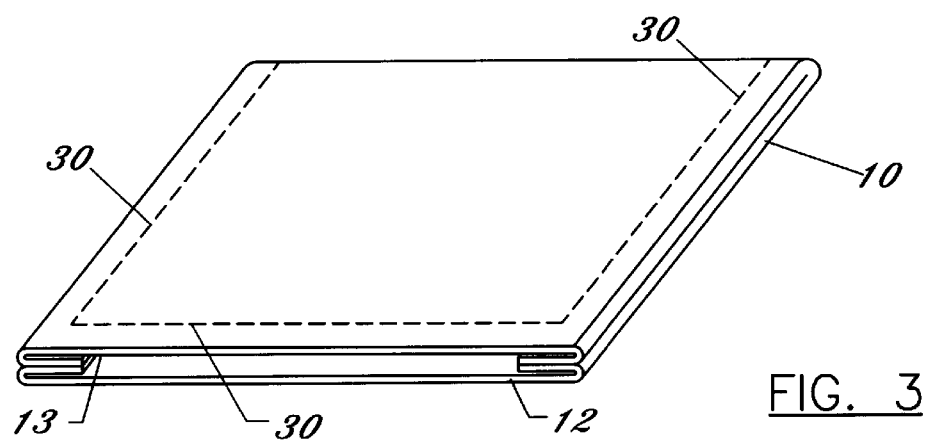
FIG. 3 is a perspective view of an inside and outside layer fastened together in accordance with the present invention.

FIG. 3 shows a perspective detail view of an outside layer 12 fastened to an inside layer 13. With reference to FIG. 2, the top folded end 18 is folded toward the bottom folded end 20 to form an inside layer 13 and an outside layer 12. The outside layer 12 is sewn to the inside layer 13 with a border stitch 30 to form a cover 10. The border stitch 30 is sewn approximately 3/32 of an inch away from the perimeter of the outside layer 12 and the inside layer 13. The outside layer 12 may also be fastened to the inside layer 13 with heat staking or glue. The outside layer 12 and inside layer 13 may be fabricated from cloth fabric, synthetic fabric, naugahyde, or leather. The diversity of cover materials provides a multitude of styling possibilities.

Figure 4:
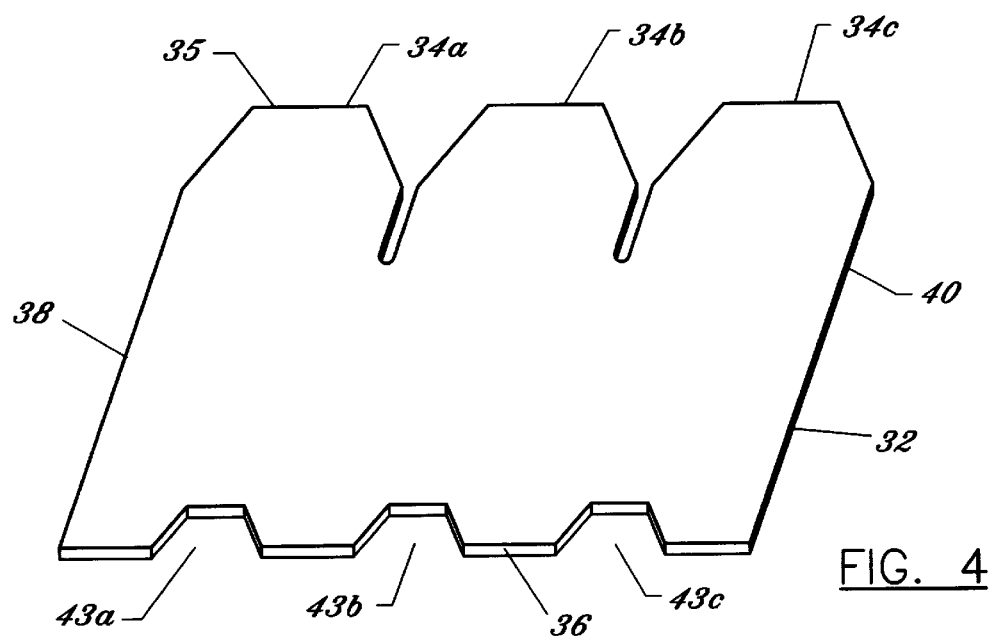
FIG. 4 is a perspective view of a pocket template used to form a plurality of pockets in accordance with the present invention.

FIG. 4 shows a perspective view of a pocket template 32 which is used to create a plurality of pockets. The pocket template 32 comprises a first end 35, a second end 36, a left edge 38, and a right edge 40. A plurality of projection tabs 34a, 34b & 34c are equally spaced apart and formed at the first end 35 of the pocket template 32. A plurality of recesses 43a, 43b & 43c are equally spaced apart and formed at the second end 36 of the pocket template 32.

Figure 5:
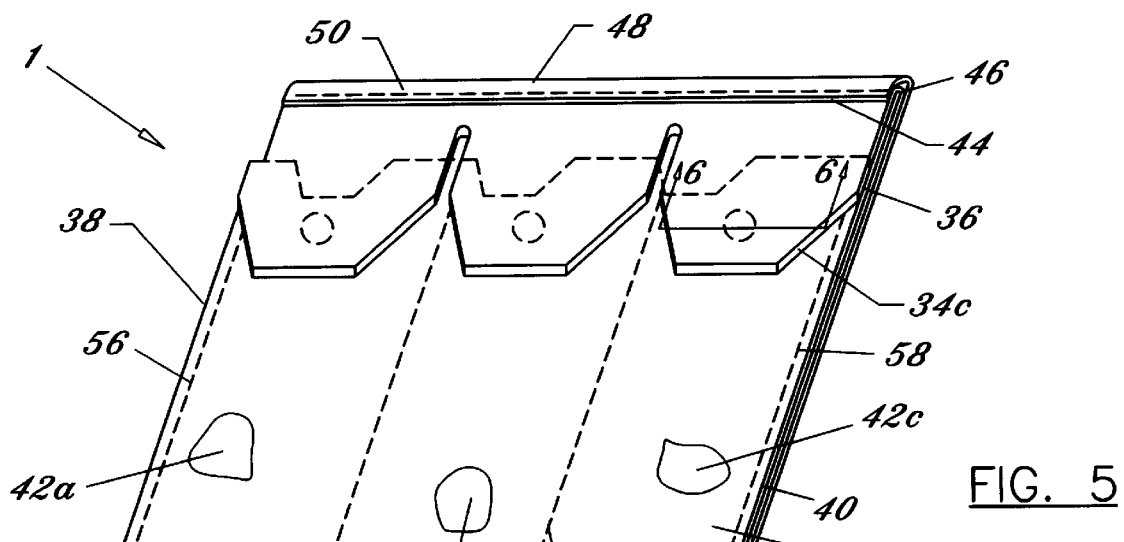
FIG. 5 is a perspective detail view of a pocket template fastened to a cover to form a multi-pocket female wallet in accordance with the present invention.

FIG. 5 shows a perspective detail view of the pocket template 32 fastened to the cover 10 to form a multi-pocket female wallet 1. With reference to FIG. 4, the second end 36 of the pocket template is folded over to form a bottom folded member 37 and the plurality of projection tabs 34a, 34b & 34c are folded over the bottom folded member 37. A plurality of pockets 42a, 42b & 42c are formed by fastening the pocket template 32 to the cover 10. A top edge 44 of the inside layer 13 is folded over and the top edge 46 of the pocket template 32 is slipped under a top folded member 48 of the inside layer 13. The top edge 44 of the inside layer 13, the top edge 46 of the pocket template 32, and the cover 10 are sewn together with a top stitch 50. The top edge 46 of the pocket template 32 may also be fastened to the cover 10 with heat staking or glue.

The left edge 38 of the pocket template 32 is sewn to a left edge 52 of the cover 10 with a left stitch 56. The right edge 40 of the pocket template 32 is sewn to a right edge 54 of the cover 10 with a right stitch 58. The pocket template 32 may also be fastened to the cover 10 at the left edge 38 and the right edge 40 with heat staking or glue. The plurality of pockets 42a, 42b & 42c are formed when the pocket template 32 and the cover 10 are sewn together with a first stitch 60 and a second stitch 62. The plurality of pockets 42a, 42b & 42c may also be formed using heat staking and glue. The fastening of the pocket template 32 to the cover 10 is such that the bottom folded member 37 of the pocket template 32 puckers upward to allow a sanitary napkin or a plurality of tampons to be inserted into one of the plurality of pockets 42a, 42b & 42c. The pocket template 32 is preferably fabricated from a transparent and flexible material.

Figure 6:
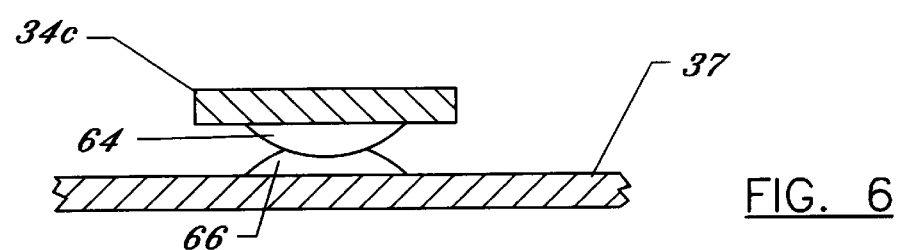
FIG. 6 is a cross sectional detail view of a tab projection and a bottom folded member which are attached together in accordance with the present invention.

FIG. 6 shows a cross sectional detail view of the tab projection 34c in FIG. 5 attached to the bottom folded member 37 with a loop fastener pad 64 and a hook fastener pad 66. The loop fastener pad 64 is attached to the tab projection 34c and the hook fastener pad 66 is attached to the bottom folded member 37. The attachment of the tab projection 34c to the bottom folded member 37 may also be implemented using a snap fastener or any other suitable removable fastening means.

Figure 7:
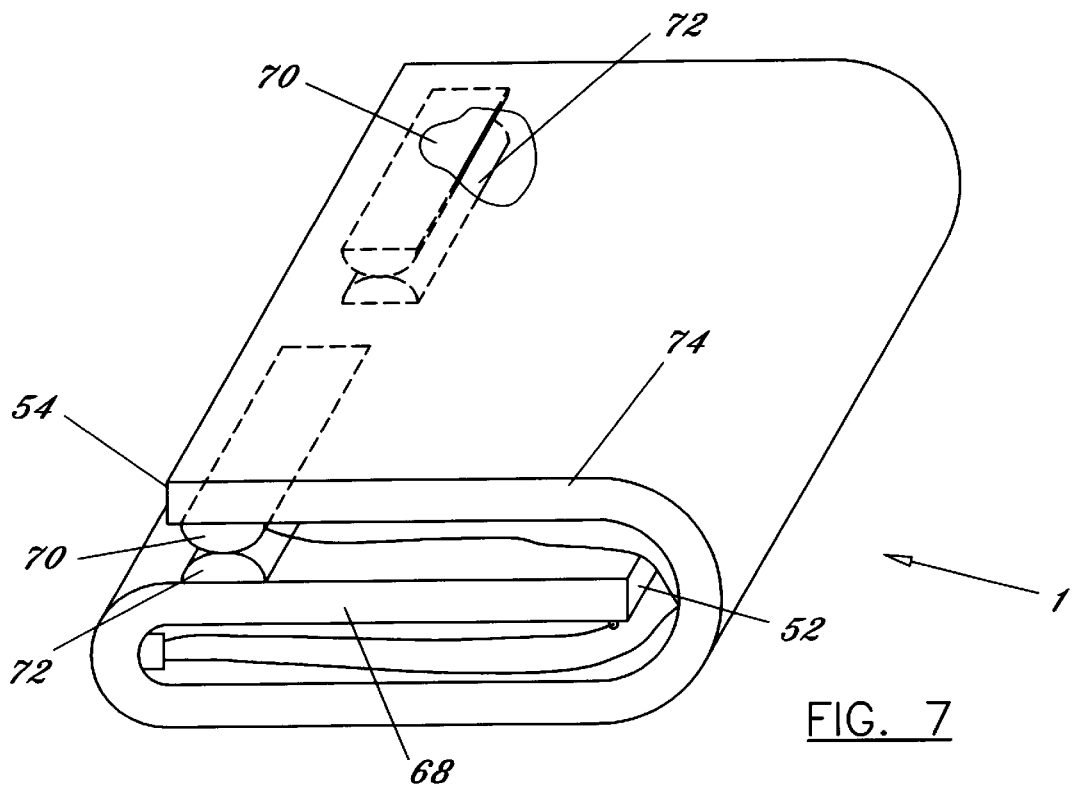
FIG. 7 is a perspective detail view of a multi-pocket female wallet which is in a folded position in accordance with the present invention.

FIG. 7 shows a perspective detail view of a multi-pocket female wallet 1 which is in a folded position. The left edge 52 of the cover 10 is folded toward the right edge 54 such that a 1/3 length of the cover 10 is folded over to form a left folded member 68. A hook fastener pad 70 is fastened to the cover 10 at the right edge 54. The right edge 54 of the cover is folded over the left folded member 68 such that a one-third length of the cover 10 is folded over the left folded member 68 to form a right folded member 74. A loop fastener pad 72 is fastened to the respective location on the left folded member 68 to retain the right folded member 74 against thereof. The attachment of the right folded member 74 to the left folded member 68 may also be implemented using a snap fastener or any other suitable removable fastening means.

Figure 8:
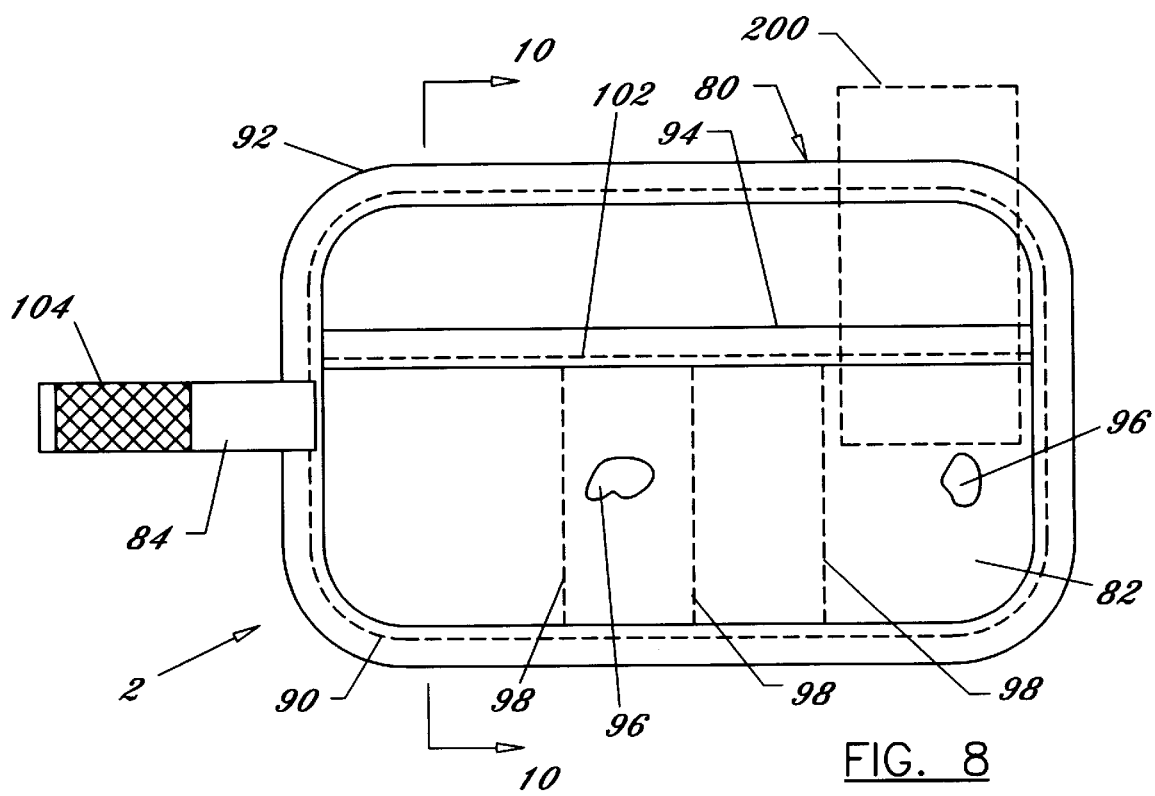
FIG. 8 is a front view of a second embodiment of a multi-pocket female wallet in accordance with the present invention.
Figure 10:
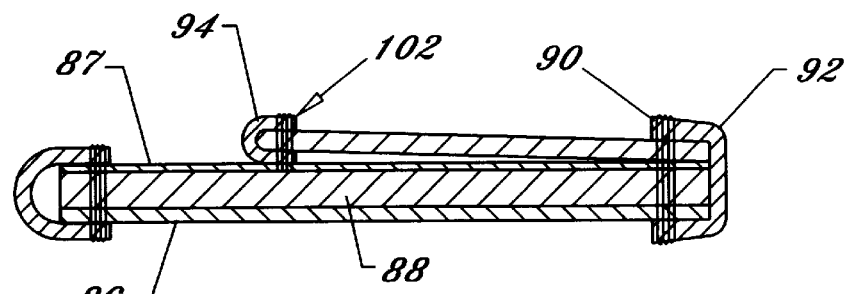
FIG. 10 is a cross-sectional view of the second embodiment of the multi-pocket female wallet in accordance with the present invention.

FIG. 8 shows a second embodiment of a multi-pocket female wallet 2 which includes a cover 80, a pocket member 82, and an attachment strap 84. With reference to FIG. 10, the cover 80 includes a first outside layer 86, an inside layer 88, and a second outside layer 87. The first and second outside layers are preferably fabricated from a durable material such as synthetic fabric, cloth fabric, naugahyde, and leather. Preferably, the first and second layers are decorated with an attractive design which would be aesthetically appealing to women. The inside layer 88 is preferably fabricated from polyester batting, other materials could also be used. The inside layer 88 gives the multi-pocket female wallet stiffness and provides a cushioned feel. The pocket member 82 is preferably fabricated from a clear plastic material, but could be fabricated from other materials. The clear plastic material allows a user to see what is inside each individual pocket 96. The first and second outside layers, inside layer 88, and pocket member 82 are preferably attached together by sewing 90 on the outside edges thereof with a surrounding seam binding 92. The top edge of the pocket member 82 is preferably terminated with a top edge seam binding 94 by sewing 102. Pockets 96 are defined by sewing 98 the cover 80 to the pocket member 82 substantially perpendicular to the length of the pocket member 82. An item 200 may be inserted into the pocket 96 from the front of the multi-purpose female wallet 2.

Figure 9:
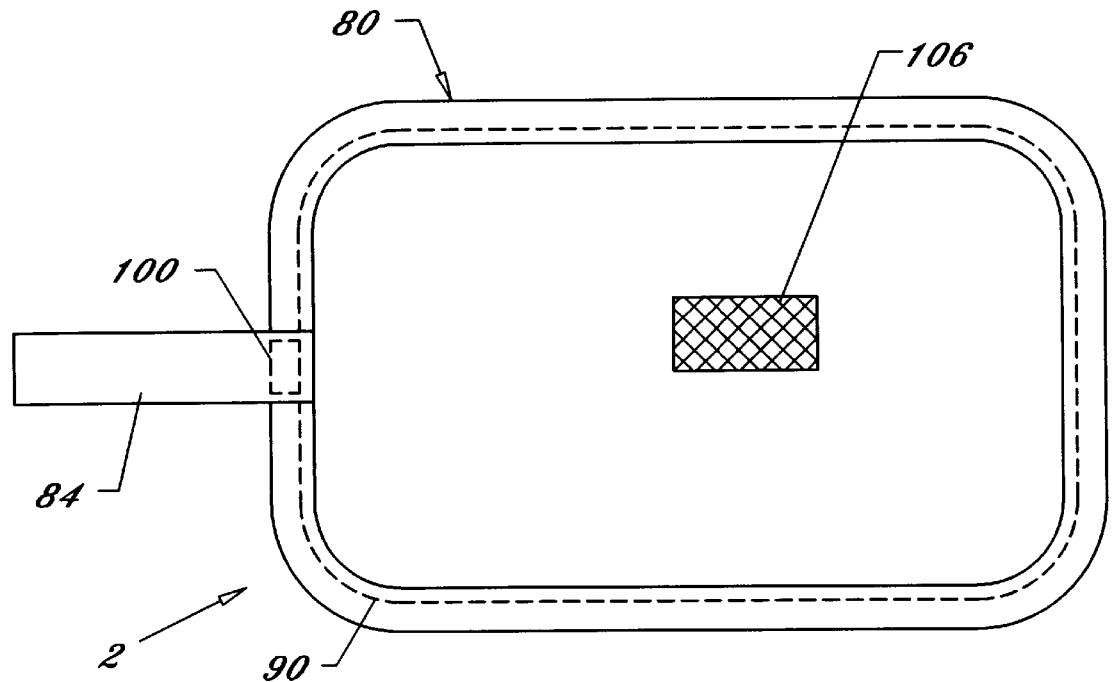
FIG. 9 is a rear view of the second embodiment of a multi-pocket female wallet in accordance with the present invention.
Figure 11:
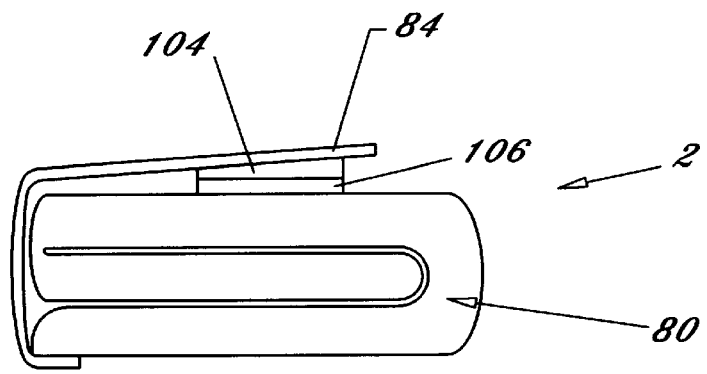
FIG. 11 is an end view of the second embodiment of the multi-pocket female wallet in a folded position in accordance with the present invention.

With reference to FIG. 9, the attachment strap 84 is preferably attached to an end of the cover 80 with sewing 100. Preferably, a loop fastener pad 104 is attached to an end of the attachment strap 84. Preferably, a hook fastener pad 106 is attached to the side opposite the pocket member 82. The positions of the hook fastener pad 106 and the loop fastener 104 may be reversed, the hook fastener pad 106 may be attached to the attachment strap 84 and the loop fastener pad 104 to the rear of the cover. Other fastener means could be used besides the hook and loop fastener pads such as snap fasteners or any other suitable removable fastening means. With reference to FIG. 11, the multi-purpose female wallet 2 is preferably folded into three substantially equal sections. The folding areas are defined by the location of the sewing 98 in the pocket member 82. The multi-purpose female wallet 2 is retained in a folded position by attaching the end of the attachment strap 84 to the hook fastener pad 106. The lengths of the loop fastener pad 104 and the hook fastener pad 106 are sufficiently long to allow the multi-purpose female wallet 2 to be retained in a folded position while fully loaded with items or while loaded with no items.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A multi-pocket female wallet for storing feminine hygiene products comprising:

a cover having an inner layer sandwiched between two outer layers;

a pocket member being fastened to said cover, a plurality of pockets being formed in said pocket member by fastening said cover to said pocket member substantially perpendicular to a length of said pocket member in at least two places;

an attachment strap being attached to said cover;

a fastening means having a first member and a second member, said first member being attached to an end of said attachment strap, said second member being attached to a rear of said cover, said attachment strap being substantially long enough to allow said cover to be folded and retained thereby with said fastening means, wherein said pockets being formed in said pocket member being sized to receive tampons and sanitary napkins.

2. The multi-pocket female wallet for storing feminine hygiene products of claim 1, further comprising:

said first member of said fastening means being a loop fastener pad, said second member of said fastening means being a hook fastener.

3. The multi-pocket female wallet for storing feminine hygiene products of claim 1, further comprising:

said inner layer being fabricated from a polyester batting.

4. The multi-pocket female wallet for storing feminine hygiene products of claim 1, further comprising:

an outside edge of said first layer, said second layer, said inner layer and said pocket member being sewn together with a surrounding seam binding.

5. The multi-pocket female wallet for storing feminine hygiene products of claim 1, further comprising:

a top edge of said pocket member being terminated with a top edge seam binding.

6. The multi-pocket female wallet for storing feminine hygiene products of claim 1, further comprising:

said plurality of pockets being formed in said pocket member by sewing said cover substantially perpendicular to the length of said pocket member.

7. The multi-pocket female wallet for storing feminine hygiene products of claim 6, further comprising:

said sewing of said pocket member to said cover being disposed such that said cover may be folded into three substantially equal sections.

8. The multi-pocket female wallet for storing feminine hygiene products of claim 1, further comprising:

said outer layers being fabricated from a durable material.

9. The multi-pocket female wallet for storing feminine hygiene products of claim 1, further comprising:

said pocket member being fabricated from a clear plastic material.

10. A multi-pocket female wallet for storing feminine hygiene products comprising:

a cover having an inner layer sandwiched between a first outer layer and a second outer layer;

a pocket member being sewn to said cover, said pocket member being fabricated from a clear plastic material, a plurality of pockets being formed in said pocket member by sewing said cover to said pocket member substantially perpendicular to a length of said pocket member, two pockets being sewn such that said cover folds into three substantially equal sections;

an attachment strap being attached to said cover;

a loop fastener pad being attached to an end of said attachment strap, a hook fastener pad being attached to a rear of said cover, said attachment strap being substantially long enough to allow said cover to be folded into three substantially equal sections and retained thereby with said fastener pads, wherein said pockets being formed in said pocket member being sized to receive tampons and sanitary napkins.

11. The multi-pocket female wallet for storing feminine hygiene Products of claim 10, further comprising:

said inner layer being fabricated from a polyester batting.

12. The multi-pocket female wallet for storing feminine hygiene products of claim 10, further comprising:

an outside edge of said first layer, said second layer, said inner layer and said pocket member being sewn together with a surrounding seam binding.

13. The multi-pocket female wallet for storing feminine hygiene products of claim 10, further comprising:

a top edge of said pocket member being terminated with a top edge seam binding.

14. The multi-pocket female wallet for storing feminine hygiene products of claim 10, further comprising:

said first and second outer layers being fabricated from a durable material.

* * * * *